United States Patent [19]

Herweh

[11] 3,933,909

[45] Jan. 20, 1976

[54] METHOD FOR PRODUCING SULFONYL SEMICARBAZIDES

[75] Inventor: John E. Herweh, Lancaster, Pa.

[73] Assignee: Armstrong Cork Company, Lancaster, Pa.

[22] Filed: July 19, 1974

[21] Appl. No.: 490,039

[52] U.S. Cl. .............................. 260/554; 260/2.5 R
[51] Int. Cl.² ............... C07C 133/02; C07C 159/00
[58] Field of Search ...................................... 260/554

[56] References Cited
UNITED STATES PATENTS

| | | | |
|---|---|---|---|
| 3,102,115 | 8/1963 | Breuer et al. | 260/554 |
| 3,152,176 | 10/1964 | Hunter | 260/554 |
| 3,344,182 | 9/1967 | Amidon | 260/554 |
| 3,546,234 | 12/1970 | Fauland | 260/554 |

OTHER PUBLICATIONS

Chemical Abstracts, Vol. 65, col. 1853yc.

*Primary Examiner*—Arthur P. Demers

[57] ABSTRACT

A new synthetic route to sulfonyl semicarbazides wherein an azobisformamide is reacted with a free sulfinic acid.

2 Claims, No Drawings

METHOD FOR PRODUCING SULFONYL SEMICARBAZIDES

BACKGROUND OF THE INVENTION

1. Field of the Invention

This invention relates to a new synthesis for sulfonyl semicarbazides which are a class of thermally labile compounds currently finding use as blowing agents.

2. Description of the Prior Art

Sulfonyl semicarbazides are presently produced by reacting the corresponding sulfonyl hydrazide with a source of cyanic acid as exemplified in U.S. Pat. No. 3,152,176-Hunter. Another method for synthesizing sulfonyl semicarbazides is disclosed in assignee's copending application Ser. No. 490,040, filing date July 19, 1974, entitled Synthesis of Sulfonyl Semicarbazides by John E. Herweh.

SUMMARY OF THE INVENTION

The process involved is the reaction of a free sulfinic acid with an alpha-carbonyl azo compound, in particular, with an azobisformamide. The yields of the sulfonyl semicarbazides are high, in fact essentially quantitative, and offer economical advantages over presently used preparatory routes for which the yields described in the literature are considerably smaller.

DESCRIPTION OF THE PREFERRED EMBODIMENT

The reaction of an alpha-carbonyl azo compound with a free sulfinic acid may be expressed by the following formula:

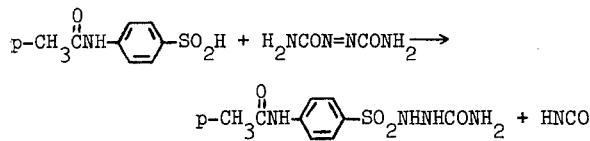

A free sulfinic acid, p-acetamidobenzenesulfinic acid is combined with a dimethyl sulfoxide solution of 1,1′ azobisformamide. Addition of the reaction mixture to water, several hours after mixing, and allowing the clear, pale yellow aqueous-dimethyl sulfoxide solution to cool to ice bath temperature results in the precipitation of a white gelatinous solid identified as 1,p-acetamidobenzenesulfonyl-1,2-bis(formamoyl)hydrazine The yield is 87.5 percent. Purification of 1,p-acetamidobenzenesulfonyl-1,2-bis(formamoyl)-hydrazine by dissolution in aqueous alkali followed by neutralization with diluted 3N hydrochloric acid results in deformamoylation and the formation (77 percent conversion) of 1,p-acetamidobenzenesulfonyl semicarbazide. Structural assignment for 1,p-acetamidobenzenesulfonyl semicarbazide was based upon elemental analysis, molecular weight, and its nuclear magnetic resonance spectrum.

As indicated above the reaction will normally be carried out in dipolar aprotic solvents inert to the starting ingredients. The dipolar aprotic solvent simply must be nonreactive with the starting ingredients. The two most commonly used dipolar aprotic solvents are dimethyl sulfoxide and dimethyl formamide although dimethyl sulfoxide is preferred, primarily due to its greater solvency for 1,1′ azobisformamide. However, any inert dipolar aprotic solvent may be used, except water, as long as it does not react with the starting ingredients since the role of a dipolar aprotic solvent is to dissolve or disperse one or more of the reactants without effecting any change in chemical composition.

The reaction should be carried out in a temperature range from 20° to 60° C. and preferably in the range of 25° to 35° C.

The concentration of the reactants in the inert dipolar aprotic solvent is usually in the range of 5 percent to 30 percent by weight of the solvent and preferably 8 percent to 15 percent by weight of the solvent.

Generally, the concentration of the reactant will depend on the solubility of the reactant in the solvent. The reaction may be carried out in any convenient manner utilizing suitable vessels or containers. One of the outstanding advantages of the present process is its simplicity, requiring mere mixing of the reactive solution, and separating out the product.

The following example illustrates the embodiment of the invention.

EXAMPLE 1

Reaction of 1,1′ azobisformamide with p-acetamidobenzenesulfinic Acid

Solutions of 1,1′ azobisformamide (2.32 g., 0.02 mol) in 50 ml of dimethyl sulfoxide and p-acetamidobenzenesulfinic acid (3.98 g., 0.02 mol) in 25 ml of dimethyl sulfoxide are combined. After several hours at room temperature, the clear, pale orange reaction mixture is added to 300 ml of water. The resulting clear, pale yellow solution is cooled to ice bath temperatures and after about 0.5 hour the mixture becomes a solid gelatinous mass.

The reaction mixture is filtered in a solid filter-cake and washed consecutively with water, alcohol, and ether to give 5.5 g. of a white solid, identified as 1,p-acetamidobenzenesulfonyl-1,2-bis(formamoyl) hydrazine. A portion (1.5 g.) of the dried reaction product (5.5 g.) is dissolved in aqueous 10 percent sodium hydroxide. Neutralization of the filtered, cleared alkaline solution with diluted 3N hydrochloric acid gives a crystalline solid, 1,p-acetamidobenzenesulfonyl semicarbazide.

What is claimed is:

1. A process for the manufacture of a sulfonyl semicarbazide of the formula

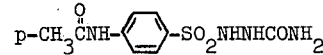

which comprises forming a precipitate by reacting in a dipolar aprotic solvent an azobisformamide of the formula $H_2NCON=NCONH_2$ with a free sulfinic acid of the formula

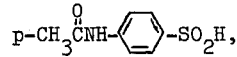

dissolving said precipitate in aqueous alkali, filtering said alkaline solution formed thereby, neutralizing said alkaline solution and recovering said sulfonyl semicarbazide.

2. The process according to claim 1 wherein said dipolar aprotic solvent is dimethyl sulfoxide.

* * * * *